US005767241A

United States Patent [19]
McEver

[11] Patent Number: 5,767,241
[45] Date of Patent: Jun. 16, 1998

[54] SOLUBLE FORM OF GMP-140

[75] Inventor: Rodger P. McEver, Oklahoma City, Okla.

[73] Assignee: The Board of Regents of The University of Oklahoma, Norman, Okla.

[21] Appl. No.: 272,224

[22] Filed: Jul. 8, 1994

Related U.S. Application Data

[63] Continuation of Ser. No. 320,408, Mar. 8, 1989, Pat. No. 5,378,464.

[51] Int. Cl.$^6$ ............................ C07K 14/00; C12N 15/09
[52] U.S. Cl. ..................... 530/350; 435/69.1; 435/325; 435/252.3; 435/254.11; 530/395; 536/235
[58] Field of Search ........................... 435/69.1, 325, 435/254.11, 252.3; 530/395, 350; 536/23.5

[56] References Cited

U.S. PATENT DOCUMENTS

| | | | |
|---|---|---|---|
| 4,605,644 | 8/1986 | Foker | 514/45 |
| 4,925,796 | 5/1990 | Bergh et al. | 435/97 |
| 5,114,842 | 5/1992 | Plow et al. | 530/388.22 |

FOREIGN PATENT DOCUMENTS 0101185  2/1984  European Pat. Off.

OTHER PUBLICATIONS

Cummings et al., Bio Essays, vol. 14, 849–856, Dec. 1992.
Issekutz, A., et al., Laboratory Invest. vol. 49, No. 6, pp. 716–724 (1983).
Stenberg, P., et al., J. Cell. Biol., vol. 101, pp. 880–886 (Sep. 1985).
Johnston, et al., Blood 70(5) Suppl. 1:352a Abstract No. 1264 (1987).
Muller–Eberhard, H., Ann. Rev. Biochem. 57:321–347 (1988).
Bevilacqua, M.P., et al., Science, vol. 242, pp. 1160–1165 (Mar. 3, 1989).
Siegelman, M.H., et al., Science, vol. 243, pp. 1165–1172 (Mar. 3, 1989).
Larsen, E., et al., Cell, vol. 59, 305–312 (Oct. 20, 1989).
Hamburger, S., et al., Blood, vol. 75, No. 3, pp. 550–554 (Feb. 1, 1990).
Johnston, G.I., et al., Cell, vol. 56, 1033–1044 (Mar. 24, 1989).
Brandley, B.K., et al., Cell, vol. 63, 861–863 (Nov. 30, 1990).
Springer, T.A., et al., Nature, vol. 349, pp. 196–197, (Jan. 17, 1991).
Goelz, S.E., et al., Cell, vol. 63, pp. 1349–1356 (Dec. 21, 1990).
Corral, L., et al., Biochem. & Biophy. Res. Comm., vol. 172, No. 3, pp. 1349–1356 (Nov. 15, 1990).
Tiemeyer, M., et al., Proc. Natl. Acad. Sci., vol. 88, pp. 1138–1142 (Feb. 1991).
Lowe, J.B., et al., Cell, vol. 63, pp. 475–484 (Nov. 2, 1990).
Walz, G. et al., Science, vol. 250, pp. 1132–1135 (Nov. 23, 1990).
Phillips, M.L., et al., Science vol. 250, pp. 1130–1131 (Nov. 23, 1990).
Bowen, B.R., et al., J. of Cell Biol., vol. 109, pp. 421–427 (Jul. 1989).
Siegelman, M.H., et al., Proc. Natl. Acad. Sci., vol. 86, pp. 5562–5566 (Jul. 1989).
Tedder, T., et al, J.Exp.Med., vol. 170, pp. 123–133 (Jul. 1989).
Lasky, L.A., et al., Cell, vol. 56, pp. 1045–1055, (Mar. 24, 1989).
Hourcade, D. et al., Advances in Immunology, vol. 45, pp. 381–415 (1989).
Johnston, G.I., et al., J. Biol. Chem., vol. 265, No. 34, pp. 21381–21385 (1990).
Watson, M.L., et al., J. Exp. Med., vol. 172, pp. 263–271 (Jul. 1990).
Hattori, R., et al., J. Biol. Chem., vol. 264, No. 15, pp. 9053–9060 (1989).
Patel, K.D., et al., J. of Cell Biol., vol. 112, No. 4, pp. 749–759 (Feb. 1991).
Bonfanti, R. et al. Blood , vol. 73, No. 5, pp. 1109–1112 (Apr. 1989).
Hattori, R., et al., J. of Biol. Chem., vol. 264, No. 14, pp. 7768–7771 (May 15, 1989).
McEver, R., et al., J. Clin. Invest., vol. 84, pp. 92–99 (Jul. 1989).
Skinner, M.P., et al., Biochem. & Biophys. Res. Comm., vol. 164, pp. 1373–1379 (1989).
Gamble, J.R., et al., Science, vol. 249, pp. 414–417 (Jul. 27, 1990).
Geng, J-G., et al., Nature, vol. 343, No. 6260, pp. 757–760 (Feb. 22, 1990).
Larsen, E., et al., Cell, vol. 63, pp. 467–474, (Nov. 2, 1990).
Moore, et al. J. Cell Biol., vol. 112, pp. 491–499 (1991).
Berkow, editor, The Merck Manual, 14$^{th}$Edition, 1982, pp. 649, 2404, 2405.
Skinner et al., Characterization of Human Platelet GMP–140 as a Heparin–Binding Protein, Biochem. Biophys. Res. Comm. 164: 1373–1379, 1989.
Harris et al "Therapeutic antibodies–the coming of age" TIBTECH 11: 42–44 (Feb. 1993).
Yeo et al., Blood, vol. 73, pp. 722–728, 1989.
McEver et al., Blood, vol. 70, 355a, 1987.
Johnston et al., J. of Cell Biology, vol. 107(6), p. 116a, 1988.
McEver et al., J. of Biological Chem., vol. 259, p. 9799, 1984.
Berman et al., J. Clin. Invest., vol. 78, p. 130, 1986.
Miereudorf et al., Methods in Enzymology, vol. 152, p. 458, 1987.
Smith et al., Science, vol. 238, p. 1704, 1987.

*Primary Examiner*—Stephen Walsh
*Assistant Examiner*—Sally P. Teng
*Attorney, Agent, or Firm*—Dunlap & Codding, P.C.

[57] ABSTRACT

The invention is directed to a purified soluble form of human granule membrane protein 140 (GMP-140) which lacks an amino acid sequence comprising a transmembrane domain and which is effective in inhibiting leukocyte adherence mediated by granule membrane protein 140. Nucleic acid encoding the soluble form of GMP-140 is disclosed.

5 Claims, 6 Drawing Sheets

SOLUBLE FORM OF GMP-140

This is a continuation of application Ser. No. 07/320,408 filed on Mar. 8, 1989, now U.S. Pat. No. 5,378,464.

The U.S. Government has rights in this invention by virtue of grants from the National Heart, Lung and Blood Institute.

BACKGROUND OF THE INVENTION

This invention is generally in the field of methods for the treatment and prevention of inflammatory responses involving GMP-140 binding reactions, particularly aggregation of platelets and leukocytes.

The adherence of leukocytes to vascular surfaces is a critical component of the inflammatory response, and is part of a complex series of reactions involving the simultaneous and interrelated activation of the complement, coagulation, and immune systems. Leukocyte adherence to vascular endothelium is a key initial step in migration of leukocytes to tissues in response to microbial invasion. Although a class of inducible leukocyte receptors, the CD11–CD18 molecules, are thought to have some role in adherence to endothelium, mechanisms of equal or even greater importance for leukocyte adherence appear to be due to inducible changes in the endothelium itself. Endothelium exposed to "rapid" activators such as thrombin and histamine becomes adhesive for neutrophils within two to ten minutes, while endothelium exposed to cytokines such as tumor necrosis factor and interleukin-1 becomes adhesive after one to six hours. The rapid endothelial-dependent leukocyte adhesion has been associated with expression of the lipid mediator platelet activating factor (PAF) on the cell surface, although direct demonstration of the adhesive role of PAF has been more difficult to demonstrate and additional mechanisms for the early adhesion have not been examined. The later cytokine-inducible endothelial adhesion for leukocytes is mediated, at least in part, by an endothelial cell receptor, ELAM-1, that is synthesized by endothelial cells after exposure to cytokines and then transported to the cell surface.

Activated platelets have also been shown to interact with both neutrophils and monocytes in vitro. The interaction of platelets with monocytes may be mediated in part by the binding of thrombospondin to platelets and monocytes, although other mechanisms have not been excluded. The mechanisms for the binding of neutrophils to activated platelets are not well understood, except that it is known that divalent cations are required. The in vivo significance of platelet-leukocyte interactions has not been studied carefully. However, in response to vascular injury, platelets are known to adhere to subendothelial surfaces, become activated, and support coagulation. Platelets and other cells may also play an important role in the recruitment of leukocytes into the wound in order to contain microbial invasion.

The complement proteins collectively play a leading role in the immune system, both in the identification and in the removal of foreign substances and immune complexes, as reviewed by Muller-Eberhard, H. J., *Ann. Rev. Biochem.* 57:321–347 (1988). Central to the complement system are the C3 and C4 proteins, which when activated covalently attach to nearby targets, marking them for clearance. In order to help control this process, a remarkable family of soluble and membrane-bound regulatory proteins has evolved, each of which interacts with activated C3 and/or C4 derivatives. This group of proteins constitutes the regulators of complement activation (RCA) gene family, reviewed by D. Hourcade, et al., *Advances in Immunology*, Volume 45, F. E. Dixon, ed., 381–416 (New York, Academic Press 1989), which are clustered at the q32 region of chromosome 1.

The coagulation and inflammatory pathways are regulated in a coordinate fashion in response to tissue damage. For example, in addition to becoming adhesive for leukocytes, activated endothelial cells express tissue factor on the cell surface and decrease their surface expression of thrombomodulin, leading to a net facilitation of coagulation reactions on the cell surface. In some cases, a single receptor can be involved in both inflammatory and coagulation processes. For example, the Mac-1 receptor on leukocytes, a member of the CD11–CD18 group, mediates phagocytosis and serves as a receptor for the degradation product of complement C3bi, is involved in one pathway of adherence of leukocytes to endothelium, mediates granulocyte aggregation, and binds coagulation Factor X.

Proteins involved in the hemostatic and inflammatory pathways are of interest for diagnostic purposes and treatment of human disorders. An example is GMP-140 (granule membrane protein 140), an integral membrane glycoprotein with an apparent molecular weight of 140,000 as assessed by sodium dodecyl sulfate polyacrylamide gel electrophoresis (SDS-PAGE).

GMP-140 was first purified from human platelets by McEver and Martin, *J. Biol. Chem.* 259:9799–9804 (1984). Monoclonal and polyclonal antibodies to GMP-140 were also prepared, as reported by McEver and Martin (1984) and P. E. Stenberg, et al., *J.Cell Biol.* 101:80–886 (1985). The protein is present in alpha granules of resting platelets but is rapidly redistributed to the plasma membrane following platelet activation, as reported by Stenberg, et al., (1985). The presence of GMP-140 in endothelial cells and its biosynthesis by these cells was reported by McEver, et al., *Blood* 70(5) Suppl. 1:355a, Abstract No. 1274 (1987). In endothelial cells, GMP-140 is found in storage granules known as the Weibel-Palade bodies.

When platelet or endothelial cells are activated by mediators such as thrombin, the membranes of the storage granules fuse with the plasma membrane, the soluble contents of the granules are released to the external environment, and membrane bound GMP-140 is presented within seconds on the cell surface. While the rapid redistribution of GMP-140 to the surface of platelets and endothelial cells as a result of activation suggests that this glycoprotein could play an important role at sites of inflammation or vascular disruption, locations where both cell types would be activated, the function of this protein has not previously been determined.

It is therefore an object of the present invention to elucidate and characterize the structure and function of GMP-140.

It is another object of the present invention to provide a surface bound ligand for GMP-140.

It is a further object of the present invention to provide a method and means for using GMP-140 and the GMP-140 ligand in modulating the immune response and the hemostatic pathway, particularly in abnormal responses involving adherence of leukocytes to platelets and endothelium.

It is a still further object of the present invention to provide a method and means for screening for defects in the immune response, especially defects in GMP-140 or in ligands for GMP-140 or related proteins.

SUMMARY OF THE INVENTION

GMP-140 is a glycoprotein present on the surface of, or secreted by, activated platelets and endothelial cells, which serves as a receptor for neutrophils and possibly other leukocytes. The glycoprotein also binds the complement protein C3b, and possibly C4b, as well as the anticoagulant cofactor, protein S. Based on the discovery of these binding functions, the method of the present invention uses either GMP-140, both the granule bound form and a newly discovered soluble form, fragments thereof, and antibodies thereto, the ligand for GMP-140, fragments thereof, and antibodies thereto, or specific sugars that are bound by GMP-140 to modulate these binding interactions in inflammatory responses, particularly in conditions associated with inappropriate adherence of leukocytes to platelets and endothelium, and the hemostatic pathway.

Labelled GMP-140 can also be used to identify patients with defects in ligands for GMP-140, and antibodies to GMP-140 or labelled nucleotide sequences derived from the gene encoding GMP-140 can be used to identify patients with defects in GMP-140. Similarly, labelled GMP-140 ligand, antibodies to GMP-140 ligand, or nucleic acid sequences encoding GMP-140 ligand can be used to detect and characterize patients having defects in GMP-140 or the GMP-140 ligand.

BRIEF DESCRIPTION OF THE DRAWINGS

FIGS. 2 and 2A are the nucleotide and deduced amino acid sequence of endothelial cell GMP-140. The nucleotide sequence is a composite of the four overlapping cDNAs lambda GMPE1-lambda GMPE4. The relative positions of each of the cDNAs are shown by the solid arrows. The dotted arrows indicate regions found in some clones, but deleted in others. The numbering of the nucleotide sequence was arbitrarily started at the first base following the adapter oligonucleotide sequence of the most 5' clone. The translated amino acid sequence of the open reading frame is given in the single-letter code. The initiating methionine was assigned to the first in-frame ATG sequence that agreed with the consensus sequence for initiation of translation. The stop codon is shown by the asterisk. The thin underlines show the matching positions of amino acid sequences determined from the N-terminus and from 26 peptides of platelet GMP-140. The signal peptide corresponds to positions −41 to −1. The putative transmembrane domain is heavily underlined. The cysteine residues are circled and potential asparagine-linked glycosylation sites (NXS/T) are shown by the dark circles. Two potential polyadenylation signals in the 3' untranslated region are underlined and overlined.

FIG. 4 is the alignment of the nine tandem consensus repeats in GMP-140. The numbers to the left of the sequence are the residue numbers at the beginning of each repeat. The boxed residues show conserved residues in at least five out of the nine repeats. The shaded boxes show the positions of conserved cysteine residues. A consensus sequence is shown below the nine aligned repeats.

DETAILED DESCRIPTION OF THE INVENTION

Figure 1:
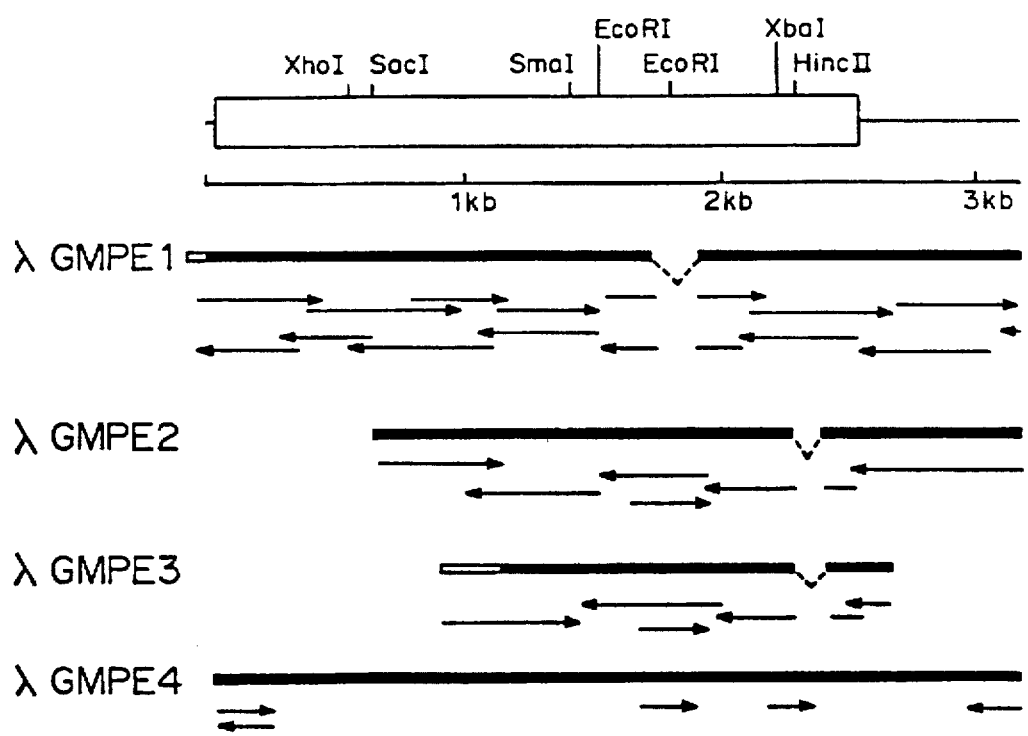
FIG. 1 is a restriction map and sequencing strategy of GMP-140 cDNAs. Thin lines represent untranslated nucleotide sequence at the 5' and 3' ends. The open box indicates the position of a long open reading frame. The regions of GMP-140 encoded by lambda GMPE1, lambda GMPE2, lambda GMPE3, lambda GMPE4, are shown by solid bars. The open bars at the 5' end of lambda GMPE1 and lambda GMPE3 probably represent cloning artifacts. The gapped areas in lambda GMPE1, lambda GMPE2 and lambda GMPE3 represent areas deleted in these clones.

The structure and biosynthesis of GMP-140 has now been analyzed in detail. The entire amino acid sequence of GMP-140 has been determined by a combination of protein sequencing of peptide fragments derived from purified platelet GMP-140 and by cloning of cDNAs encoding GMP-140 from a human endothelial cell cDNA library. Based on the structure and on functional studies, GMP-140 acts as a receptor for neutrophils and possibly other leukocytes, and interacts with complement protein C3b and the anticoagulant cofactor protein S.

Cloning of the gene for GMP-140 was first reported by G. I. Johnston, R. G. Cook and R. P. McEver in Abstract 1238 Supplement II *Circulation* 78(4) (October 1988). Oligonucleotides were prepared based on N-terminal amino acid sequencing of GMP-140 peptides and used to screen a human endothelial cell cDNA library. A 3.0 kb clone was isolated which encoded a protein of 727 amino acids. An N-terminal domain of 158 residues containing many cysteines, lysines, and tyrosines, which is similar to the asialo glycoprotein receptor, is followed by an EGF-type repeating domain structure, and eight tandem repeats of 62 amino acids each, except for the sixth tandem repeat which has 70 amino acids. The repeats are homologous to those found in a family of proteins that include proteins regulating C3b and C4b, but are unique in having six conserved cysteines per repeat instead of the typical four. These are followed by a 24 amino acid transmembrane region and a 35 amino acid cytoplasmic tail.

As reported by Johnston, et al., in Abstract 1218, *Blood* Suppl. 72, 327a (November 1988), the gene for GMP-140 has been localized to the long arm of chromosome 1, where genes for a number of C3b/C4b regulating proteins have been mapped.

As also reported, there appears to be at least two forms of the protein encoded by related genes: a soluble form and a membrane or granule bound form. The gene for the soluble protein is characterized by a 186 bp insertion, encoding a ninth 62 amino acid tandem repeat, between the sixth and seventh tandem repeats of the sequence encoding the granule-bound glycoprotein. Further, the soluble protein gene has a 120 bp deletion that removes 40 amino acids including the transmembrane region.

The conclusion that GMP-140 serves as receptor for the adherence of leukocytes to activated endothelial cells and platelets is based on several observations. First, the rapid appearance of GMP-140 on the surface of endothelium stimulated with thrombin or histamine parallels the inducible adherence of neutrophils to endothelium stimulated with these agonists. In addition, platelets interact with neutrophils or monocytes only after activation with agonists such as thrombin which cause redistribution of GMP-140 to the cell surface; platelet agonists such as ADP which do not induce degranulation and surface expression of GMP-140 do not cause platelets to adhere to leukocytes. Second, in endothelium, GMP-140 is concentrated in postcapillary venules, where ELAM-1 is concentrated. The concentration of both proteins in this region is important because postcapillary venules are the predominant sites for binding of leukocytes prior to their migration across the endothelium into the tissues. Third, purified GMP-140 coated on tissue culture microtiter wells mediates specific adherence of purified neutrophils to the wells. Fourth, polyclonal antibodies to GMP-140 block 60–90% of the adherence of neutrophils to cultured human umbilical vein endothelial cells stimulated with histamine. Fifth, the cDNA-derived amino acid sequence of GMP-140 indicates that its structure is remarkably similar to that of ELAM-1, an endothelial cell protein already known to bind neutrophils.

Other studies have demonstrated that GMP-140 binds to C3b, a complement system protein, and protein S, an anticoagulant cofactor protein. GMP-140 shares sequence homology with the plasma protein C4b-binding protein (C4bp), which not only interacts with the plasma protein C4b but also with protein S.

The present invention provides a method of modulating the hemostatic and inflammatory responses in a patient wherein a therapeutically effective amount of a compound capable of blocking leukocyte recognition of GMP-140 is administered to the patient. In one embodiment, GMP-140 or GMP-140 specific monoclonal antibodies which are capable of blocking leukocyte recognition of GMP-140, or therapeutic compositions derived therefrom, is administered to the patient. In another embodiment, ligand for GMP-140, or fragments thereof, or monoclonal antibodies to the ligand, is administered to the patient. In yet another embodiment, the specific sugar portion of the ligand that is bound by GMP-140 is administered to the patient.

The following methods are used for the production and characterization of GMP-140, antibodies thereto, and nucleotide sequences encoding GMP-140.

Production of Monoclonal Antibodies

Production and characterization of monoclonal antibodies to GMP-140 (formerly known as glycoprotein IIa) is described by McEver and Martin in *J. Biol. Chem.* 259(15) 9799–9804 (1984). Briefly, hybridomas producing antiplatelet antibodies are generated by fusion and screened with a radioimmune binding assay, as reported by McEver, et al., *J. Biol. Chem.* 258, 5269–5275 (1983) and McEver, et al., *J. Clin. Invest.* 66, 1311–1318 (1980). Monoclonal IgG is purified from mouse ascites by ammonium sulfate precipitation and DEAE-cellulose chromatography. Fab fragments are prepared by papain digestion and isolated from Fc fragments and undigested IgG by DEAE-cellulose chromatography.

For therapeutic use, large quantities of GMP-140 specific monoclonal antibodies are produced by hybridomas formed by the fusion of an anti-GMP-140 antibody producing cell and a cell line which imparts long term tissue culture stability to the hybrid cell lines, using methods known to those skilled in the art (Kohler and Milstein, *Nature*, 256:495–497 (1975) and Kennet, et al., *Monoclonal Antibodies* pp 365–367 (Plenum Press, N.Y., 1980)). The anti-GMP-140 antibody producing cell will usually be a B lymphocyte obtained from an animal or human who has developed an immune response to GMP-140 naturally, as a result of a pathogenic process or as a consequence of having been immunized with material containing GMP-140 such as activated platelets or a biological preparation containing GMP-140. The stabilizing cell can be a cell of B lymphocyte lineage such as a B lymphoblastoid cell line or a plasmacytoma cell such as a myeloma cell, a malignant antibody producing cell.

The resulting clones are screened for production of antibody reactive with GMP-140 positive platelets or biological preparations containing GMP-140. Those which secrete antibodies of the appropriate reactivity and specificity are cloned to yield a homogeneous cell line secreting anti-GMP-140 antibody.

Another method of forming an anti-GMP-140 producing cell line is by transformation of antibody producing cells. For example, an anti-GMP-140 producing B lymphocyte may be infected and transformed with a virus such as Epstein-Barr virus in the case of B lymphocytes to yield anti-GMP-140 producing cells, using the method of Kozbor and Roder, *Immunology Today*, 4(3): 72–79 (1983). Alternatively the B lymphocyte may be transformed by a transforming gene or transforming gene product.

The GMP-140 specific monoclonal antibodies are produced in large quantities by injecting anti-GMP-140 antibody producing hybridomas into the peritoneal cavity of mice or other appropriate animal hosts and, after an appropriate time, harvesting the resulting ascitic fluid which contains a high titer of antibody and isolating the monoclonal anti-GMP-140 antibody. Allogeneic or xenogeneic hybridomas are injected into immunosuppressed, irradiated or athymic nude mice. Alternatively, the antibodies may be produced by culturing anti-GMP-140 producing cells in vitro and isolating secreted monoclonal anti-GMP-140 antibodies from the cell culture medium.

Platelets

Platelets are obtained by differential centrifugation of blood from normal volunteers and anticoagulated with 0.1 volume of 3.8% sodium citrate or by gel filtration in Tyrode's buffer (0.138M NaCl, 0.029 KCl, 0.012M NaHCO$_3$, 0.036M NaH$_2$PO$_4$—H$_2$O, pH 7.4). See McEver, et al., *J. Biol. Chem.* 258, 5269–5275 (1983). Other procedures are known to those skilled in the art, such as Stenberg, et al., (1985).

Protein Iodination

Proteins and antibodies are radiolabeled with Na$^{125}$I using Enzymobeads (Biorad Laboratories) followed by gel filtration on a Sephadex G-25 column to remove free Na$^{125}$I.

Isolation of GMP-140 from Platelets

Two methods have been used to isolate GMP-140 from platelets. In one method, antibody to GMP-140 is bound to cyanogen bromide-activated Sepharose 4B, which has been prewashed in 1 mM HCl and equilibrated in 0.1M NaHCO$_3$, 0.5M NaCl, pH 8.3. Antibody and Sepharose (15 mg antibody: 1 g Sepharose) are mixed for 16 h at 4° C., the resin poured into a column and washed sequentially with 0.1M glycine NaOH, pH 11.5; 1M Tris-HCl, pH 7.4; 0.15M Na acetate, pH 4.3; and 0.15M NaCl, 0.02M Tris-HCl, pH 7.4.

Platelets, isolated by differential centrifugation and resuspended in 0.15M NaCl, 0.02M Tris-HCl, pH 7.4, 0.4 mM PMSF are sonicated four times at 48 watts for 15 sec at 4° C. and centrifuged at 2,000×g for 15 min. The supernatant is centrifuged at 100,000×g for 60 min at 4° C., the resulting pellet is resuspended in 0.15M NaCl, 0.02M Tris-HCl, pH 7.4, 2 mM DIFP, 1% Lubrol PX, and the resolubilized protein centrifuged at 100,000×g for 60 min at 4° C. to remove insoluble material.

The GMP-140 containing supernatant is first chromatographed on Sepharose 4B in the same buffer but with 0.1% Lubrol PX, then the eluant is affinity purified by chromatography on antibody bound Sepharose, washed with 0.15M NaCl, 0.02M Tris-HCl, pH 7.4, 0.1% Lubrol PX; 0.5M NaCl, 0.02M Tris-HCl, pH 7.4, 0.1% Lubrol PX; 1M NaCl, 0.02M Tris-HCl, pH 7.4, 0.1% Lubrol PX; and 0.15M NaCl, 0.02M Tris-HCl, pH 7.4, 0.1% Lubrol PX; and eluted with 0.1M glycine NaCl, pH 11.5, 0.5 mM PMSF, 0.1% Lubrol PX. The protein is then dialyzed at 4° C. against 0.15M NaCl, 0.02M Tris-HCl, pH 7.4, 0.5 mM PMSF, 0.1% Lubrol PX.

This method is modified as follows to obtain increased yields of functionally active GMP-140.

Wash: Outdated human platelet packs (100 units) obtained from a blood bank and stored at 4° C. are pooled, adjusted to 5 mM EDTA at pH 7.5, centrifuged at 4,000 rpm for 30 min in 1 liter bottles, then washed three times with 1 liter of 0.1M NaCl, 20 mM Tris pH 7.5 (TBS), 5 mM EDTA, 5 mM benzamidine.

The pellets are then resuspended in a minimum amount of wash buffer and made 1 mM in DIFP, then frozen in 50 ml screwtop tubes at −80° C.

Extraction: The frozen platelets are thawed and resuspended in 50 ml TBS, 5 mM benzamidine, 5 mM EDTA pH 7.5, 100 μM leupeptin. The suspension is frozen and thawed two times in a dry ice-acetone bath using a 600 ml lyophilizing flask, then homogenized in a glass/teflon mortar and pestle and made 1 mM in DIFP. The NaCl concentration is adjusted to 0.5M with a stock solution of 4M NaCl. After stirring the suspension at 4° C., it is centrifuged in polycarbonate tubes at 33,000 rpm for 60 min at 4° C. The supernatant (0.5M NaCl wash) is removed and saved; this supernatant contains the soluble form of GMP-140. Care is taken not to remove the top part of the pellet with the supernatant. The pellets are then homogenized in extraction buffer (TBS, 5 mM benzamidine, 5 mM EDTA, pH 7.5, 100 μM leupeptin, 2% Triton X-100). After centrifugation at −19,500 rpm for 25 min at 4° C., the supernatant is removed. The extraction procedure is repeated with the pellet and the supernatant is combined with the first supernatant. The combined extracts, which contain the membrane form of GMP-140, are adjusted to 0.5M NaCl.

Purification: The soluble fraction (0.5M NaCl wash) and the membrane extract (also adjusted to 0.5M NaCl) are absorbed with separate pools of the monoclonal antibody S12 (directed to human GMP-140) previously coupled to Affigel (Biorad) at 5 mg/ml for 2 h at 4° C. After letting the resins settle, the supernatants are removed. The S12 Affigel containing bound GMP-140 is then loaded into a column and washed overnight at 4° C. with 400 ml of 0.5M NaCl, 20 mM Tris pH 7.5, 0.01% Lubrol PX.

Bound GMP-140 is eluted from the S12 Affigel by one of two procedures. The procedures are the same for the soluble and membrane forms, except that Lubrol PX is omitted from the buffers used in purification of the soluble form.

Elution procedure A: The column is eluted with 100 ml of 80% ethylene glycol, 1 mM MES pH 6.0, 0.01% Lubrol PX. Peak fractions with absorbance at 280 nm are pooled.

Elution procedure B: The column is eluted with 100 ml of cold 1M NaCl, 1.5M guanidine-HCl, 20 mM Tris pH 7.5, 0.01% Lubrol PX. Peak fractions absorbing at 280 nm are pooled.

Concentration: Eluates from either elution procedure are dialyzed against TBS (with 0.05% Lubrol for the membrane fraction), then applied to a Mono Q column (FPLC from Pharmacia). The concentrated protein is step eluted with 2M NaCl, 20 mM Tris pH 7.5 (plus 0.05% Lubrol PX for the membrane fraction). Peak fractions are dialyzed into TBS pH 7.5 (plus 0.05% Lubrol PX for the membrane fraction).

Protein Sequencing

GMP-140 was isolated and purified from human platelet membranes. On one occasion it was reduced under an atmosphere of nitrogen by the addition of dithiothreitol (20 mM, final concentration) and alkylated in the presence of iodoacetamide (Bray, et al., Proc.natl.Acad.Sci.USA 83:1480–1484 (1986). It was then digested with trypsin. The resultant peptides were isolated by two-step, reverse-phase, high performance liquid chromatography (HPLC) using previously described methods (Rosa, et al., Blood 72:593–600 (1988). On a second occasion, GMP-140 was reduced and alkylated in the presence of 50 μCi [$^{14}$C]-iodoacetamide (Amersham) before unlabeled iodoacetamide was added. It was then gel-purified (Bray, et al., 1986) and electroeluted into 25 mM Tris, 192 mM glycine, pH 8.0, containing 0.1% Triton X-100 (Jacobs and Clad, Anal. Biochem. 154: 583–589 1986). One milligram of GMP-140 was digested with endoglycosidase Glu-C (Boehringer-Mannheim Biochemicals) at a ratio of 1:10 w/w at 37° C. After 6 hr, an equal amount of protease was added and the mixture was incubated for a further 14 hr at 37° C. Peptides were isolated by reverse-phase HPLC as described by Rosa, et al., (1988), except that the initial separation on the C4 HPLC column was carried out using ammonium acetate buffer and the second separation on the C18 HPLC column was carried out using trifluoroacetic acid. Fractions containing the purified peptides were concentrated to 50 μl and kept frozen before sequencing. Amino acid sequences were determined from the N-terminus of the intact protein and from the peptides by using a gas-phase protein sequencer [Applied Biosystems Model 470A] (Rosa, et al., 1988). Cysteine residues were identified by their elution profile on the HPLC system used by the protein sequencer, and confirmed by measuring $^{14}$C radioactivity in duplicate aliquots from each sequencing cycle. The peptide sequences are shown in Table 1.

cDNA Screening

Based upon a portion of the amino acid sequence of peptide 16B (underlined in Table 1), two pools of a 35-mer oligonucleotide probe, designed according to codon usage tables (Lathe, J. Mol. Biol. 183:1–12(1985)), were synthesized. The complementary strand was used to allow hybridization to RNA by Northern blotting. Inosine was used in one position because the third base of a glycine codon showed no preferential nucleotide. The sequences of the pools were:

POOL 1:

5'-GC TGT CCA CTG ICC GAG GTT GTC ACA GCG CAC AAT-3'
                    A                           A
                    C                           T
                                                C

-continued

POOL 2:

5'-GC TGT CCA CTG ICC GAG GTT GTC ACA TCT CAC AAT-3'
          A                              C
          C

On Northern blots, both oligonucleotide probes hybridized to a 3.6-kb transcript from poly(A)$^+$ RNA isolated from CHRF-288 cells, a leukemia cell line with megakaryocyte-like properties (Witte, et al., *Cancer* 58:238–244 (1986)). Pool 2 probes hybridized more strongly and was therefore used to screen a cDNA library by standard procedures (Maniatis, et al., *Molecular Cloning: A Laboratory Manual* (Cold Spring Harbor Laboratory, Cold Spring Harbor, N.Y. 1982). Approximately 1.4 million recombinant phage from an unamplified human endothelial cell lambda gt11 library (Ye, et al., *J.Biol.Chem.* 262:3718–3725 1987) were plated out on *E. coli* Y1088 at a density of 200,000 plaques per 230-mm square plate of NZCYM agar. Duplicate nylon filters (Hybond-N, Amersham) were lifted, denatured, neutralized, and incubated at 42° C. for 24 hr in prehybridization solution containing 5×standard saline citrate (SSC) [1×SSC is 150 mM NaCl, 15 mM sodium citrate], 5×Denhardt's solution [0.02% Ficoll, 0.02% polyvinylpyrrolidone, 0.02% BSA], 0.2% SDS, and 200 μg/ml herring sperm DNA. The 35-mer oligonucleotide probe 2 was end-labeled with [gamma-$^{32}$P]ATP by 5'-polynucleotide kinase and was added to prehybridization solution to give a specific activity of 1×10$^6$ cpm/ml. The filters were hybridized at 42° C. overnight and the final washing conditions were 2×SSC, 0.1% SDS at 52° C. Positive plaques, identified by autoradiography of filters, were rescreened twice using the same probe and purified. The positive cDNA inserts were isolated from an agarose gel following digestion of phage DNA with SalI or EcoRI. Either enzyme could be used because, during the library construction, cDNAs were ligated to adapter oligonucleotides containing a SalI restriction site as well as an EcoRI site (Ye, et al., 1987). The inserts were subcloned into pIB120 (IBI Biotechnologies, Inc.) for restriction mapping and DNA sequencing, and into M13mp18 (New England Biolabs) for DNA sequencing. Sequencing in M13mp18 was carried out by the dideoxy chain-termination procedure (Sanger, et al., *Proc.Natl.Acad.Sci.USA* 74:5463–5467 (1977) using either modified T7 polymerase (Sequenase from United States Biochemicals) or Klenow fragment of DNA polymerase (Bio-Rad Laboratories). Priming was performed with either the M13 universal primer or with 17-mer oligonucleotides designed from cDNA sequence. Double-stranded plasmid DNA, isolated by a standard alkaline-lysis mini-prep method (Maniatis, et al., 1982), was sequenced using the method described by Kraft, et al., *Biotechniques* 6:544–547 (1988). The plasmid templates were primed with either universal primer, reverse primer (International Biotechnologies, Inc.), or 17-mer oligonucleotides.

Isolation and Characterization of cDNA Clones

Three clones, positive after tertiary screening, were plaque purified, and phage DNA was prepared. The inserts from the clones, designated lambdaGMPE-1–lambdaGMPE3, were subcloned into plasmids and sequenced using the scheme shown in FIG. 1. The DNA sequences of all three clones contained long open reading frames which overlapped. The translated sequence of the longest clone, lambdaGMPE1, contained an amino acid sequence which matched the N-terminal amino acid sequence of intact platelet GMP-140 but which lacked an in-frame ATG, which encodes a methionine to initiate translation, 5' to this sequence.

Figure 2:
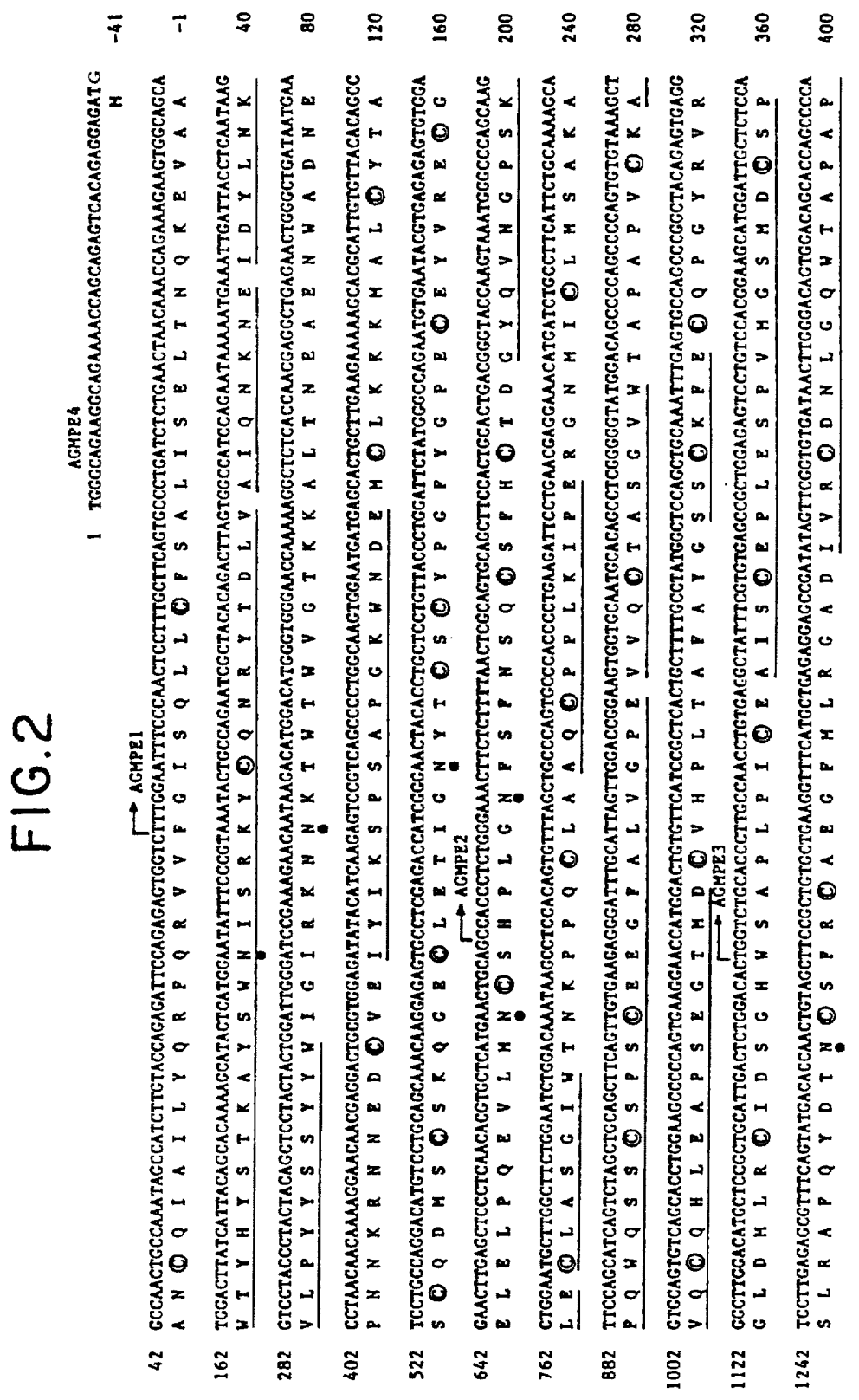
Figure 2A:
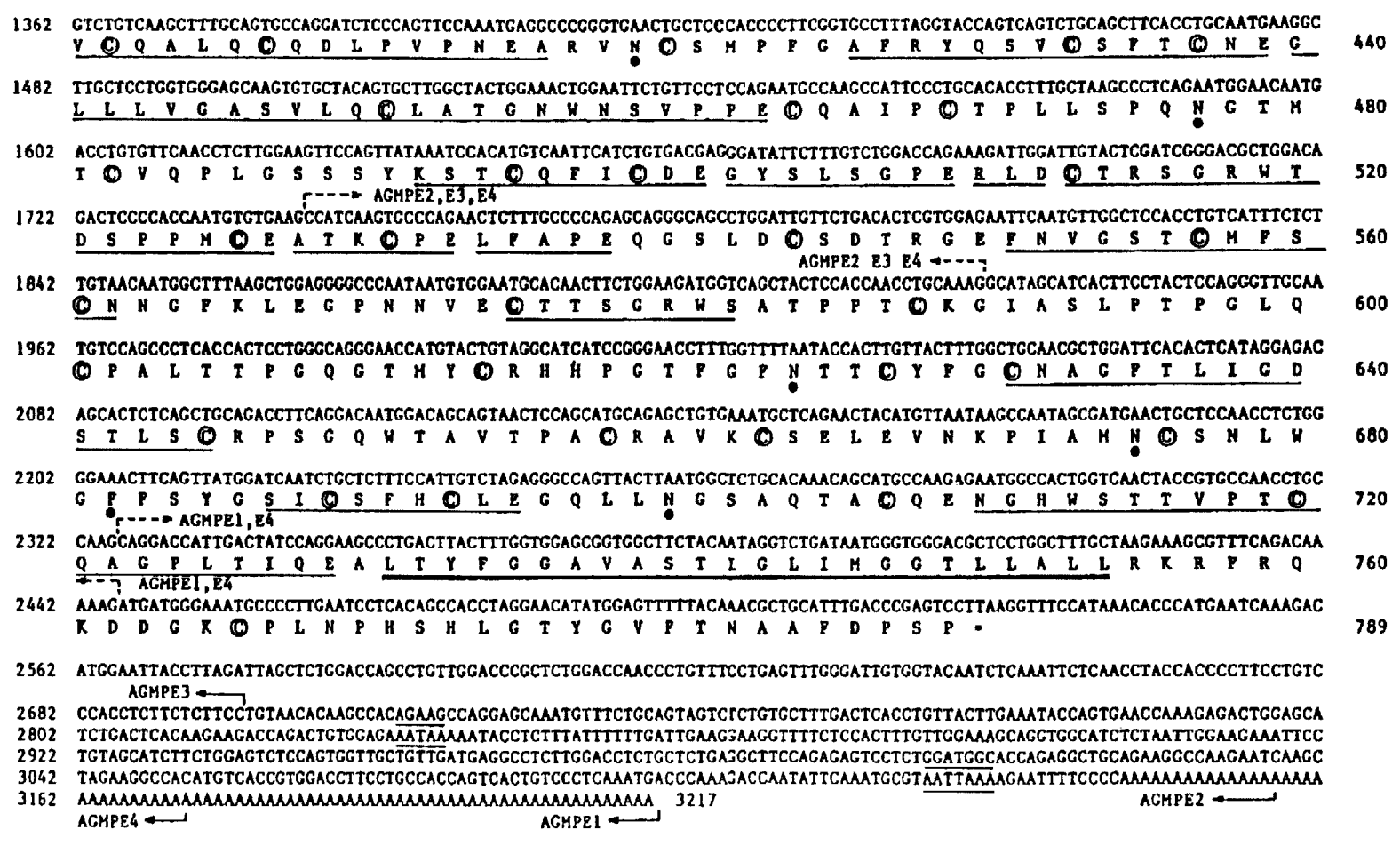

To identify full-length cDNAs, 1.4 million recombinant phage of the now amplified endothelial-cell cDNA library were rescreened with a 1-kb SmaI fragment from the 5' end of lambda GMPE1 (FIG. 1). Of the 55 positive clones identified, five were purified. DNA sequence from the 5' end of one of these new clones, designated lambdaGMPE4, matched the 5' end of lambdaGMPE1, except that the first 88 bp were not found within the first 140 bp of lambdaGMPE1. Translation of the sequence of lambdaGMPE4 showed that there was an in-frame ATG sequence beginning at nucleotide 39. The sequence of the 5' end of lambdaGMPE4 was also found in the other four clones obtained in the second screening of the cDNA library, suggesting that it was the correct sequence and that the first 140 bp of lambdaGMPE1 was a cloning artifact. FIGS. 2 and 2A are a composite sequence of the four clones, with 91% of the sequence derived from lambdaGMPE1.

The composite sequence predicts a 5' untranslated region of 38 bp, followed by an open reading frame of 2490 bp coding for a protein of 830 amino acids, then a 3' untranslated sequence of 614 bp including two potential polyadenylation signals of AATAAA and AATTAAA. The latter signal precedes a 12-bp sequence, then a poly(A)$^+$ tail of 75 bp. The nucleotide sequence GxxATGG, surrounding the first in-frame ATG beginning at base 39, agrees with the consensus sequence for initiation of protein translation (Kozak, *Nucl. Acids Res.* 12:857–872, 1984). Therefore the first amino acid was assigned to this codon.

When compared to the sequence of the other clones, there was a 186-bp segment deleted from lambda GMPE1, corresponding to nucleotides 1744 to 1929 (FIGS. 1, 2 and 2A). A 120-bp deletion was also found in lambda GMPE2 and lambda GMPE3 (nucleotides 2326 to 2445). Eight single-base substitutions (confirmed by sequencing both strands of the cDNAs) were found in the first three clones. Three were silent substitutions, changing the third degenerate base of a codon. The other five produced conservative amino-acid changes.

Northern Blot Analysis

Total RNA was prepared from the human megakaryocyte-like leukemia cell lines CHRF-288 (Witte, et al., *Cancer* 58:238–244 (1986)) and HEL (Papayannopoulou, et al., *J. Clin. Invest.* 79:859–866 (1987)), the myeloid cell line K562 (Lozzio and Lozzio, *Blood* 45:321–334 (1975)), human umbilical vein endothelial cells, the EA.hy 926 hybrid endothelial cell line (Edgell, et al., *Proc.Natl.Acad.Sci.USA* 80:3734–3737 (1983), human platelets, and the Daudi B-cell line (Klein, et al., *Cancer Res.* 28:1300–1310 (1969)) by an acid-guanidinium-phenol-chloroform procedure (Chomczynski and Sacchi, *Anal.Biochem.* 162:156–159 (1987)). Both HEL cells and K562 cells were treated with Phorbol myristate acetate (PMA) for 48 hr. to induce differentiation before RNA was prepared. Poly(A)$^+$ RNA was isolated from total RNA by oligo-dT cellulose chromatography (Davis, et al., *Basic Methods in Molecular Biology* (Elsevier, New York 1986). Total or poly(A)$^+$ RNA was electrophoresed on a 1% agarose gel containing formaldehyde, then transferred to a Hybond-N nylon membrane by standard procedures (Maniatis, et al., *Molecular Cloning, A Laboratory Manual* (Cold Spring Harbor, N.Y. 1982). The membrane was prehybridized in 5×SSC, 5×Denhardt's solution, 0.2% SDS, and 200 μg/ml herring sperm DNA for oligonucleotide probes, or in 5×Denhardt's solution, 50% formamide, 10% dextran sulfate, and 200 μg/ml herring sperm DNA for cDNA probes. Oligonucleotide probes were labeled by the procedure described above, and cDNA probes were random-labeled with a α-$^{32}$P dCTP using the Klenow fragment of DNA polymerase in a commercial kit (Boehringer-Mannheim Biochemicals). Probes were hybridized overnight at 42° C. at a specific activity of at least 1×10$^6$ cpm/ml. The filters to which the oligonucleotides were hybridized were washed with 2×SSC, 0.5% SDS for 20-min periods at increasing temperatures up to 52° C., whereas those used with the cDNA probes were washed with 0.2×SSC, 0.1% SDS at temperatures up to 60° C. and were exposed to film (X-OMAT AR, Kodak) at −80° C. Molecular weight markers of lambda DNA (Boehringer-Mannheim Biochemicals), electrophoresed in parallel with the RNA samples, were visualized by including labeled lambda/ HindIII DNA fragments (Bethesda Research Laboratories) [5×10$^5$ cpm/ml] in the hybridization solution.

Southern Blot Analysis

Human placental genomic DNA (intact or digested with EcoRI, BamHI, and BamHI/HindIII) were obtained from Oncor. Intact DNA was also digested with PstI, TaqI, and XbaI. Ten μg of each digested DNA was electrophoresed on a 1.5% agarose gel and transferred to a nylon membrane using a modification of the procedure of Reed and Mann, Nucl.Acids Res. 13:7207–7221 (1985). Briefly, the gel was soaked in 0.2M HCl for 10 minutes, rinsed four times in water, and transferred to a nylon membrane in 0.4M NaOH buffer for 1 hr, then in 20×SSC overnight. The DNA was fixed to the membrane by exposure to UV light and hybridized with cDNA as described for the Northern blot. Lambda/HindIII fragments and ΦX174/HaeIII fragments (Bethesda Research Laboratories) were used as standards and were visualized by including randomly labeled DNA fragments of lambda and ΦX174 (5×10$^5$ cpm/ml) in the hybridization solution.

Computer Analysis

DNA and protein sequence were analyzed using the Genetics Computer Group software package of the University of Wisconsin (Devereux, et al., Nucl.Acids Res. 12:387–395 (1984)). The amino acid sequence of GMP-140 was compared with the published sequences of other proteins contained in the National Biomedical Research Foundation (NBRF) database (Release 16.0; 3/88).

The cloning and characterization of GMP-140 and the genes encoding soluble and granule-bound GMP-140 are described in detail as follows.

TABLE 1

| Peptide Sequences From Platelet GMP-140 | |
|---|---|
| N-Term | WTYHYSTKAYSWhISRKYsQNRYTDLV |
| 1A | AVQCQHLEAPSEGT(t)(D) |
| 2A | xFQHQS(S)CSFSCEEGFALVGPE |
| 3A | nSCKFE |
| 3B | AIKCPE |
| 4A | xQCP(P)LKIx(E) |
| 5A | SICSFHCLE |
| 5B | AFRYQSVCSFTCNE |
| 6A | IYIKSPSAPGKWNDE |
| 7A | CTTSGRWS |
| 7B | GYSLSGPE |
| 7C | KSTCQFICDE |
| 8A | CTRSGRWTDSPPMCE |

TABLE 1-continued

| Peptide Sequences From Platelet GMP-140 | |
|---|---|
| 8B | GYQVNGPSKLE |
| 9A | LFAPE |
| 10A | LVAIQNKNE |
| 11A | VVQxTASGVW |
| 11B | RLDC |
| 12A | CNAGFTLIGD |
| 13A | STLSC |
| 14A | CLASGIW |
| 14B | NGHWxTTVPTCQAGPLTIQE |
| 15A | FNVGSTCHFSCN |
| 16A | AISCEPLESPVHGSMDC(S)(P) |
| 16B | IVRCDNLGQWTAPAPVCQALQCQDLPVPxxA |
| 17A | xDYLNKVLPYYSSYYW |
| 18A | GLLVGASVLQCLATGNWNSVPPE |

Listed are the amino acid sequences of the N-terminus of intact GMP-140 (N-Term) and of 26 different peptides. Amino acid residues are in single-letter code. Ambiguous residues are in parentheses; undetermined residues are denoted as "x". Lower-case letters indicate four amino acid assignments which differed from those predicted by cDNA sequence analysis. The 35-mer oligonucleotide used to screen the cDNA library was designed from the sequence underlined in peptide 16B.

The Translated GMP-140 Sequence Identifies Six Structural Domains

Figure 3:
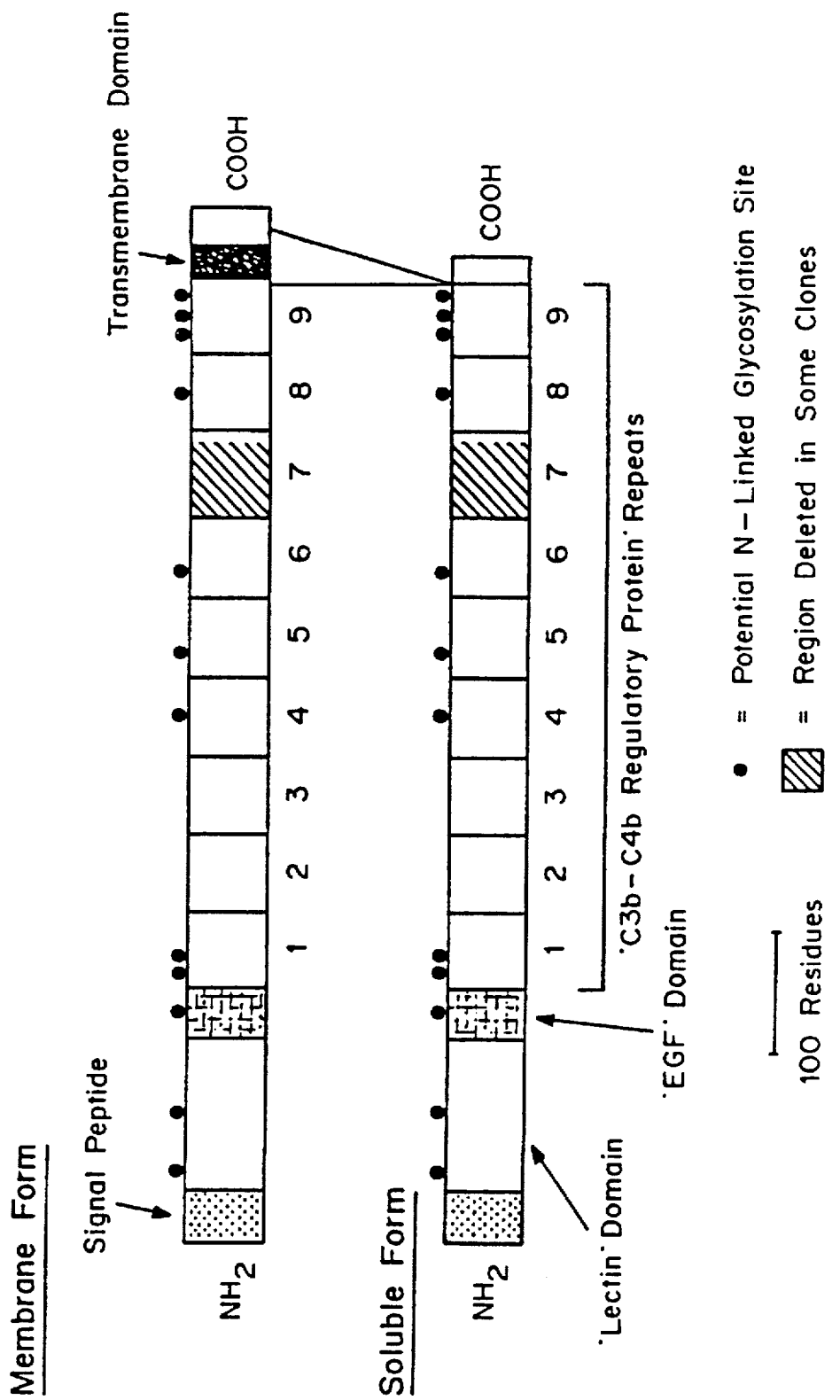
FIG. 3 illustrates the structural domains of GMP-140. The organization of GMP-140 is shown schematically, with the N- and C- termini labelled. The boundaries of each domain were selected based upon either the properties of the sequence or its similarity to domains in other known proteins. Potential asparagine-linked glycosylation sites are shown by the dark circles. The upper portion of the figure represents the form of GMP-140 that is predicted to be membrane-bound in clones lambda GMPE1 and lambda GMPE4. The lower portion of the figure represents the soluble form of GMP-140 predicted by lambda GMPE2 and lambda GMPE3, which contains a 120-bp deletion encompassing the transmembrane domain. The area indicated by the diagonal shading represents a 186-bp deletion in lambda GMPE1.
Figure 5:
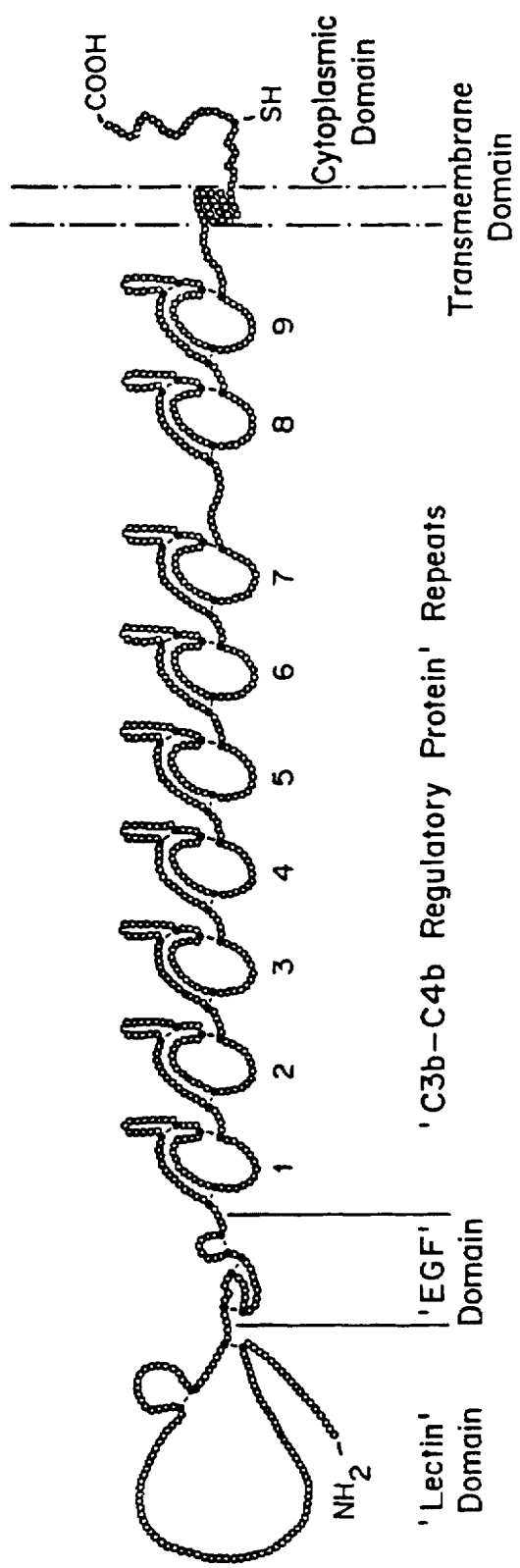
FIG. 5 is the proposed folding pattern of the domains in GMP-140. The formation of disulfide bridges in each domain was assumed to be the same as the pattern experimentally determined in similar regions of other proteins. The cysteine residues are shown by the dark circles and the potential free sulfhydryl in the cytoplasmic domain is indicated by —SH.

The predicted amino acid sequence of endothelial cell GMP-140 suggests the presence of six different structural domains, shown schematically in FIG. 3. One of these regions, a 24-residue hydrophobic segment near the C-terminus (heavily underlined in FIGS. 2 and 2A), is characteristic of membrane spanning domains. Most of the protein is located on the N-terminal side of this domain and appears to be extracytoplasmic, i.e., facing the lumen of the secretory granule, or, following activation of the cell, exposed to the extracellular environment. This conclusion is based on studies in which the majority of GMP-140 could be proteolytically removed from the surface of activated platelets.

Beginning at the N-terminus, the first domain contains 41 residues (labeled −41 to −1 in FIGS. 2 and 2A) and has the characteristic features of a signal peptide. These include several positively charged amino acids, followed by a hydrophobic domain and then a region rich in polar residues. The small uncharged residues found at positions −3 and −1 are typical of those found at sites of cleavage by signal peptidase. In addition, the amino acid sequence of the N-terminus of platelet GMP-140 matches the deduced endothelial cell sequence at 25 out of 27 positions from residues 1 to 27 (FIGS. 2 and 2A).

Following the signal peptide, the translated cDNA sequence predicts a mature protein of 789 residues. Comparison of the sequences of the platelet GMP-140 peptides (Table 1) to the deduced endothelial cell sequence showed that 337 of 341 assigned amino acids match (underlined in FIGS. 2 and 2A), suggesting that both cell types synthesize the same protein. The four differences in amino acid sequence probably represent errors due to weak signals on the protein sequencer, although they may be due to polymorphisms. The amino acid composition of the deduced sequence, $Asp_{24}$, $Asn_{45}$, $Thr_{54}$, $Ser_{68}$, $Glu_{41}$, $Gln_{36}$, $Pro_{58}$, $Gly_{64}$, $Ala_{53}$, $Cys_{56}$, $Val_{33}$, $Met_{12}$, $Ile_{24}$, $Leu_{60}$, $Tyr_{28}$, $Phe_{30}$, $His_{21}$, $Lys_{30}$, $Arg_{26}$, $Trp_{17}$, is in agreement with the experimentally determined value for purified platelet GMP-140. The predicted molecular weight of 86,244 daltons is also similar to the apparent Mr of deglycosylated platelet protein determined by SDS-PAGE. There are 12 potential asparagine-linked glycosylation sites having the consensus sequence NxS/T (FIGS. 2 and 2A). All are located on the extracytoplasmic portion of the molecule and all appear to be glycosylated based on the carbohydrate composition of platelet GMP-140. The mature protein contains 65 cysteines accounting for 8% of the total amino acids. Most of these are predicted to be organized into disulfide bridges since only a small amount of carboxymethyl cysteine can be identified in samples of nonreduced GMP-140 treated with iodoacetamide.

The second domain begins at residue 1 and encompasses the first 118 amino acids of the mature protein. This region is rich in lysine (12%), tyrosine (10%), asparagine (13%), and tryptophan (6%) residues. The boundary of this domain is based upon the computer-predicted similarity between this region and sequences found in several other proteins in a variety of species. This region of GMP-140 is designated as a "lectin" domain, since many of the proteins containing this motif bind carbohydrate. When this region of GMP-140 is aligned with five other proteins in which analogous domains show the greatest sequence similarity, identities range from 23% to 30%. A number of conserved residues are found, including five of seven tryptophans, all four cysteines, and several glycine, asparagine, aspartic acid, and proline residues.

The third domain, which begins at residue 119, has a sequence of 40 amino acids that contains six cysteines. Comparison of this region of GMP-140 to sequences in the NBRF database reveals many proteins that contain the same arrangement of cysteines. The first protein described with this motif is the epidermal growth factor (EGF) precursor, which contains ten homologous copies (Gray, et al., *Nature* 303:236–240 (1983); Scott, et al., *Nature* 221:236–240 (1983).

Figure 4:
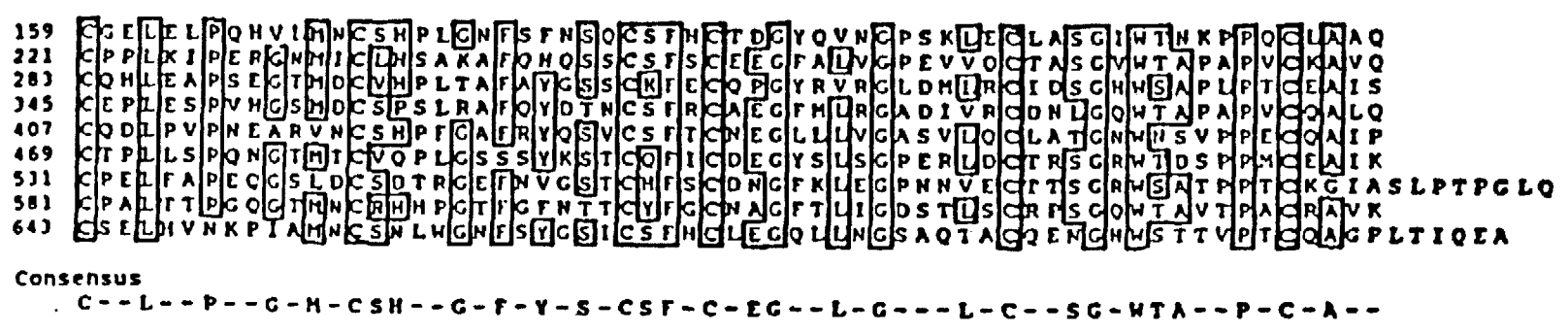

The fourth domain, which begins at residue 159, consists of nine tandem consensus repeats, each containing 62 amino acids; in addition, extensions of eight and four residues, respectively, are found at the ends of the seventh and ninth repeats (FIG. 4). The boundaries of this domain are set arbitrarily at the first cysteine of the initial repeat and at the last residue before the putative transmembrane domain. A consensus sequence shows that many amino acids occur in at least five out of the nine repeats. All repeats contain six conserved cysteines, three glycines, and one tryptophan, phenylalanine, proline, and leucine. The cysteine residues are arranged in a different motif than the six cysteines found in the "EGF" domain. The repeats are 31% to 56% identical to each other at the amino acid level and 42% to 62% identical at the nucleotide level. No gaps are required to maximize the alignment among the repeats. Comparison of this region of GMP-140 to sequences in the NBRF database demonstrated that similar repeating units are found in at least 15 other proteins. These proteins can be grouped into three categories.

Proteins in the first group regulate the activity of the complement system in plasma or on cell surfaces, either by dissociating nascent C3b–4b or C4b–C2a complexes, or by serving as cofactors for the proteolytic cleavage of C3b or C4b by factor I. The genes for all these proteins have been mapped to a tightly linked region on the q32 region of chromosome 1 and have been termed the regulators-of-complement-activation (RCA) gene family.

The second group consists of complement proteins that bind to C3b or C4b during the assembly of multiprotein complexes. Proteins in the third group have diverse functions not known to involve interaction with the complement system. These proteins include the plasma protein β-2 glycoprotein 1 and the b chain of factor XIII. Alignment of the consensus sequence for the GMP-140 repeats with those found in the RCA gene family demonstrates that the repeats in GMP-140 share four invariant cysteines as well as conserved tryptophan, proline, glycine, and phenylalanine residues. However, the first half of the GMP-140 repeats are unique in containing two additional invariant cysteines, as well as conserved methionine, leucine, glycine, and serine residues not found in repeats of other proteins.

The fifth domain, beginning at residue 731, is the 24-residue putative transmembrane domain. Following this is the sixth domain, a presumed cytoplasmic segment of 35 residues that begins with several highly charged residues and ends at the C-terminus of the protein at residue 789. There are possible phosphorylation sites at serine, threonine, and tyrosine residues, as well as a cysteine that might undergo posttranslational modification.

Two different in-frame deletions are identified among the sequences of the four endothelial-cell clones examined in detail. The first deletion, found in lambda GMPE1 (FIGS. 1, 2, 2A and 3), is 186 bp. This deletion removes 62 amino acids from the seventh consensus repeat and predicts a protein containing eight instead of nine repeats. The sequences of four peptides (labeled 3B, 7A, 9A, and 15B in Table 1) match sequence in this repeat, suggesting that the nine-repeat form exists in platelets as well as in endothelial cells. The second deletion, found in clones lambda GMPE2 and lambda GMPE3, is 120 bp, which removes 40 amino acids just after the end of the ninth repeat. The region deleted includes the transmembrane domain and the first few residues of the cytoplasmic domain. The remaining 28 residues at the C-terminus are predicted to continue just after the ninth repeat. A hydrophilicity plot (Kyte and Doolittle, *J.Mol.Biol.* 157:105–132 (1982) predicts that this form of GMP-140 is soluble.

Northern and Southern Blot Analysis

Total or poly(A)$^+$ RNA isolated from several different cell types was examined by Northern blot analysis for the presence of GMP-140 transcripts. A 3.6-kb transcript was identified in RNA from CHRF-288 cells and PMA-treated HEL cells (two human leukemia cell lines with features of megakaryocytes), human umbilical vein endothelial cells, EA.hy 926 cells (a hybrid line developed by fusing human umbilical vein endothelial cells with a carcinoma cell line), and human platelets. No transcripts were detected in poly (A)$^+$ RNA from Daudi cells (a human B cell line) or PMA-stimulated K562 cells (a human myeloid cell line).

Southern blot analysis of human genomic DNA digested with different restriction enzymes indicated that a full-length GMP-140 cDNA hybridized to a limited number of fragments. The probe hybridized at high stringency to three EcoRI-digested bands that totaled 9.2 kb in size, three XbaI-cut bands totaling 16.9 kb, four TaqI-cut bands totaling 10.8 kb, and five BamHI/HindIII-cut bands (the smaller bands identified after a longer exposure) totaling 9.3 kb. A larger 18-kb band seen in the TaqI and BamHI/HindIII digests may represent incompletely digested DNA.

Isolation and Characterization of the GMP-140 Ligand

Ligand for GMP-140 can be isolated, characterized, antibodies made, and utilized in a manner similar to that for the GMP-140 protein or fragments and antibodies.

Cellular ligands for GMP-140 are isolated using standard biochemical procedures known to those skilled in the art, as described above with reference to GMP-140. The preferred cell to use for isolating ligand is the neutrophil. However, the same methods can be used with any cell having ligands for GMP-140. These cells are identified by assays in which the cells are bound to immobilized GMP-140, or in which labelled GMP-140 is bound to the cells.

The preferred approach is to isolate ligand using affinity chromatography. GMP-140, purified as described above, is coupled to an affinity support such as Affigel (Biorad Laboratories) or cyanogen bromide activated agarose (Pharmacia Fine Chemicals, Piscataway, N.J.) using the manufacturer's instructions. Neutrophils, or a membrane fraction from neutrophils, are lysed in non-ionic detergent such as Triton X-100 or Lubrol PX in a physiological buffer at pH 7.4. After centrifugation to remove insoluble material, the cell lysate is applied to the GMP-140 affinity column pre-equilibrated in lysis buffer. The column is washed with buffer and bound ligand eluted using, for example, increasing or decreasing salt buffers, ethylene glycol, increasing or decreasing pH buffers, buffers containing a chaotrophic agent such as guanidine hydrochloride, or a buffer containing specific sugars that inhibit the lectin-dependent interaction between GMP-140 and its ligand.

Alternatively, monoclonal antibodies to the ligand are prepared by immunizing mice with human neutrophils or a neutrophil membrane fraction. Hybridomas producing monoclonal antibodies reacting with neutrophils are screened for inhibition of binding of neutrophils, or other cells containing GMP-140 ligands, to purified GMP-140. The blocking monoclonal antibodies are used to isolate putative GMP-140 ligand by affinity chromatography, as described above, except that the monoclonal antibody is coupled to Affigel or the agarose instead of the GMP-140.

Isolated ligand for GMP-140 can be analyzed using methods known to those skilled in the art. The ligand is presumed to be a glycoprotein, based on work on the high endothelial receptors for homing receptors, described below. The apparent molecular weight can be measured by SDS-PAGE or calculated from the amino acid composition. The total carbohydrate composition can be determined by quantitative methods and use of endo- and exoglycosidases. Biosynthesis of the molecule can be examined with pulse-chase studies of neutrophils, or other cells, labelled with [$^{35}$S]methionine or cysteine, or with tritiated mannose, fucose, or other sugars. The biosynthetic studies with labelled sugars are particularly useful for determining the precise carbohydrate structures in the ligand which may be critical for recognition by GMP-140. Amino acid sequence can be obtained from the N-terminus of the intact protein or from proteolytic fragments separated by high performance liquid chromatography or other biochemical procedures. The cDNA encoding the protein part of the ligand can be isolated and sequenced by standard techniques. The preferred method is to screen a cDNA library prepared from human neutrophils, or other cells containing GMP-140 ligands, with labelled oligonucleotides synthesized according to amino acid sequence of the ligand. Should the ligand prove to be another structure such as a glycolipid, rather than a glycoprotein, the above procedures would be modified accordingly.

Antibodies and cDNA probes for the isolated ligand molecules are prepared as described with reference to the GMP-140.

The cDNA-derived primary structure of GMP-140 provides several insights into functions for GMP-140 in the vascular system. The most remarkable observation is the striking structural similarity of GMP-140 to two other receptors found on vascular cells which have been recently cloned.

The first of these similar receptors is ELAM-1. ELAM-1 is an endothelial cell protein that is not present in unstimulated endothelium. However, when endothelium is exposed to cytokines such as tumor necrosis factor or interleukin-1, the gene for ELAM-1 is transcribed, producing RNA which in turn is translated into protein. The result is that ELAM-1 is expressed on the surface of endothelial cells 1-4 hours after exposure to cytokines, as reported by Bevilacqua et al., Proc.Natl.Acad.Sci.USA 84:9238-9242 (1987) (in contrast to GMP-140, which is stored in granules and presented on the cell surface within seconds after activation). ELAM-1 has been shown to mediate the adherence of neutrophils to cytokine-treated endothelium and thus appears to be important in allowing leukocytes to migrate across cytokine-stimulated endothelium into tissues. The cDNA-derived primary structure of ELAM-1 indicates that it contains a "lectin" domain, an EGF domain, and six (instead of the nine in GMP-140) repeats similar to those of complement-regulatory proteins, a transmembrane domain, and a short cytoplasmic tail. There is extensive sequence homology between GMP-140 and ELAM-1 throughout both proteins, but the similarity is particularly striking in the lectin and EGF domains.

The structural similarities of GMP-140 and ELAM-1 suggest that GMP-140 mediates the adhesion of neutrophils and possibly other leukocytes to platelets and endothelial cells induced by "rapid" activators such as thrombin and histamine. In this scenario, GMP-140 and ELAM-1 are related proteins with related function. They differ, however, in their cell distribution, in their kinetics of expression, and possibly in their specificity for particular sets of leukocytes or for particular molecules on the surface of leukocytes.

Based on the similarities between GMP-140 and ELAM-1, functional studies were performed which demonstrate that purified GMP-140 binds to neutrophils. Platelet GMP-140, purified by the revised protocol as described earlier, was coated on the bottom of microtiter wells of tissue culture plates, in concentrations ranging from 0.5 to 50 µg/ml. The wells were blocked in Hanks balanced salt solution containing 5 mg/ml of human serum albumin (HBSS/A). Human neutrophils, purified by gradient fractionation on Mono-poly (Flow Laboratories) and resuspended in HBSS/A at $10^6$ cells/ml were then added (0.1 ml of cells per well). After incubation for 30 min at room temperature, the wells were gently washed and bound cells were identified by microscopy. The number of neutrophils bound to the wells was minimal on control wells blocked with HBSS/A alone or wells precoated with control proteins such as fibrinogen or gelatin. However, neutrophil binding increased dramatically with increasing concentrations of GMP-140 applied to the wells. This binding was specifically blocked with goat polyclonal IgG directed toward human GMP-140, but not by nonspecific goat IgG. The binding was also blocked by addition of EDTA to the neutrophil suspension, indicating that the binding of neutrophils to GMP-140 appears to require divalent cations. This is significant because the lectins with structures similar to the lectin domain in GMP-140 require calcium ions for carbohydrate binding, as does the lectin activity of the homing receptor, described below.

In other studies, monolayers of human umbilical vein endothelial cells were stimulated with thrombin or histamine followed by the addition of neutrophils in HBSS/A to demonstrate that the neutrophils adhered to endothelial cells having GMP-140 on their surface. The neutrophils adhered rapidly (within 5–10 minutes) to the endothelial cells. Adherence was blocked 60–90% by simultaneous addition of goat polyclonal IgG to GMP-140, but not by nonspecific IgG.

The second molecule with overall structural similarity to GMP-140 is a homing receptor found on lymphocytes. Homing receptors are lymphocyte surface structures that allow lymphocytes to bind to specialized endothelial cells in lymphatic tissues, termed high endothelial cells or high endothelial venules (reviewed by Yednock and Rose, *Advances in Immunology*, vol. 44, F. I. Dixon, ed., 313–378 (Academic Press, New York 1989). This binding allows lymphocytes to migrate across the endothelium into the lymphatic tissues where they are exposed to processed antigens. The lymphocytes then re-enter the blood through the lymphatic system. A homing receptor that directs lymphocytes to peripheral lymph nodes has been cloned (Laskey et al., CITE 1989).

The homing receptor contains a lectin domain, an EGF domain, two complement-binding repeats, a transmembrane domain, and a short cytoplasmic tail. The homing receptor also shares extensive sequence homology with GMP-140, particularly in the lectin and EGF domains. The literature on homing receptors suggests that they interact with molecules on high endothelial venules by a true lectin-dependent process, and that binding can be inhibited by addition of certain sugars to the incubation medium, particularly polymerized forms of mannose-6-phosphate. In addition, pretreatment of high endothelial venules with neuraminidase prevents lymphocyte binding. This suggests that the homing receptor functions as a lectin that recognizes carbohydrate moieties on a molecule on the high endothelial venule; these moieties are likely to include sialic acid that can be cleaved by neuraminidase and to be part of a glycoprotein in at least some cases (Nakache, et al., *Nature* 337:179–181 (1989).

Comparisons of GMP-140 with other Receptors

The discovery of a lectin domain in the homing receptor strengthens the likelihood that cell-cell interactions between lymphocytes and lymphatic high endothelial cells are mediated by carbohydrate recognition. Given the remarkable sequence similarity of the lectin domains of the homing receptor, ELAM-1, and GMP-140, it seems very probable that the binding of leukocytes to ELAM-1 and GMP-140 also involve the recognition of carbohydrates on leukocyte molecules by the lectin domains of ELAM-1 and GMP-140. If neutrophil adhesiveness to GMP-140 is mediated by carbohydrate, then in vivo infusion of these sugars may reduce neutrophil adhesiveness. The carbohydrate recognition should be sufficiently specific so that infusion of a specific sugar structure would inhibit leukocyte interactions with platelets and endothelial cells without affecting other potential lectin-mediated interactions in the vascular system. Based on known lectin interactions, for example, studies conducted on the homing receptor, mannose-6-phosphate, fructose-1-phosphate, fucoidin, and polyphosphomonoester core of yeast wall mannan from *Hansenula holstii*, are illustrative of sugars that could be bound to either GMP-140, or its ligand, to inhibit GMP-140 mediated leukocyte adhesion. In vivo, care must be taken to infuse sugars that are highly specific and of high affinity, at concentrations that are sufficiently low to avoid complications of hyperosmolarity.

The interaction of leukocytes to activated platelets and endothelium can also be inhibited by antibodies to GMP-140, soluble fragments of GMP-140 containing the leukocyte binding domain, which is likely to include the lectin region of the molecule, the ligand for GMP-140, the GMP-140 binding portions of the ligand, or antibodies to the ligand.

In addition to mediating the interaction of leukocytes with activated platelets and endothelial cells, GMP-140 may also be involved in platelet aggregation and perhaps in platelet-endothelial interactions. The mechanism for initiation of platelet aggregation requires the binding of adhesive proteins such as fibrinogen to the integrin glycoprotein (GP) IIb–IIIa on the platelet surface (reviewed in Phillips, *Blood* 71:831–843 (1988). Binding of thrombospondin to a distinct receptor may also be involved. In studies employing frozen thin-section immunocytochemistry of platelet aggregates, immunoreactive GPIIb–IIIa, as well as the adhesive ligands fibrinogen, fibronectin, von Willebrand factor, and thrombospondin, were localized to regions of contact between platelets that developed 5–60 sec after stimulation of the cells with thrombin. However, these proteins could not be detected 5–15 min after stimulation in the long contact zones between closely apposed, irreversibly aggregated platelets (Isenberg et al., *Blood* (Suppl. 1) 70:351a (abstract 1987). In contrast, immunoreactive GMP-140 was present in regions of cell contact at both early and late time points.

This suggests the possibility that GMP-140 stabilizes irreversible platelet aggregates after initial cell-cell contact is initiated by binding of adhesive proteins to GPIIb–IIIa. If so, inhibition of this interaction could enhance the ability of competitive antagonists of the GPIIb–IIIa-adhesive protein interaction to block platelet aggregation. An example of a clinical situation where this might be useful would be in the prevention of re-occlusion of a coronary artery by platelets following thrombolytic therapy.

Binding of C3b by GMP-140

The nine tandem consensus repeats in GMP-140 are similar to repeating units found in proteins that bind the complement components C3b and C4b, suggesting that GMP-140 might also bind these proteins. This possibility was strengthened by the observation that the gene for GMP-140 is located on the long arm on human chromosome 1. This is the same region on which a number of the genes for complement-regulatory proteins are located. Studies have now shown that purified GMP-140 does bind C3b. It is postulated that GMP-140 might provide the surface of activated platelets and endothelial cells with additional protection from damage by deposition of C5b-9 membrane attack complexes of complement. Alternatively, GMP-140 might bind C3b or C4b to facilitate clearance of circulating immune complexes or the adherence of opsonized cells. One possibility is that C3b or C4b is bound to the CR1 receptor on circulating neutrophils. The bound C3b could then interact with GMP-140, resulting in a second lectin-independent mechanism for adherence of leukocytes to activated platelets and endothelium. If this mechanism is operative, then interactions of leukocytes with activated platelets and endothelial cells could also be inhibited with antibodies to the C3b–C4b-binding region of GMP-140, or soluble fragments of GMP-140 containing this region.

Binding of Protein S by GMP-140

One of the complement-regulatory proteins containing repeating units homologous to those in GMP-140 is C4b-binding protein (C4bp). In addition to binding C4b, this plasma protein also binds the anticoagulant cofactor, protein S. Protein S serves as a cofactor for the anticoagulant serine protease, activated protein C. Activated protein C proteolytically inactivates coagulation Factors V and VIII, thus suppressing the coagulation cascade. Binding of protein S to C4bp blocks the anticoagulant functions of protein S. The dual binding specifications of C4bp for C4b and protein S suggested that GMP-140 might also bind protein S. This possibility was especially attractive because certain vascular cell receptors such as Mac-1 on monocytes can have several different functions related to both inflammation and coagulation. A number of studies have now shown that purified GMP-140 does interact with purified protein S. Initial studies suggest that the binding facilitates the anticoagulant cofactor function of protein S. Accordingly, infusion of soluble fragments of GMP-140 containing the protein S-binding site might serve as novel anticoagulants.

Diagnosis and Treatment of Disorders of the Inflammatory Response System

An inflammatory response may cause damage to the host if unchecked, because leukocytes release many toxic molecules that can damage normal tissues. These molecules include proteolytic enzymes and free radicals. Examples of pathological situations in which leukocytes can cause tissue damage include injury from ischemia and reperfusion, bacterial sepsis and disseminated intravascular coagulation, adult respiratory distress syndrome, tumor metastasis, and atherosclerosis.

Since GMP-140 has several functions related to leukocyte adherence, inflammation, and coagulation, clinically, several compounds which interfere with binding of GMP-140, including GMP-140 or antibodies thereto, or the GMP-140 ligand or antibodies thereto, can be used to modulate an immune response.

For example, leukocyte adherence can be inhibited by infusion of monoclonal antibodies directed against GMP-140 that competitively block the adherence of leukocytes to GMP-140 on activated platelets and endothelial cells. Alternatively, soluble fragments of GMP-140, produced by genetic engineering, can be used to competitively inhibit leukocyte adherence by competitively binding to GMP-140 receptors on the surface of leukocytes. This kind of therapy would be particularly useful in acute situations where effective, but transient, inhibition of leukocyte-mediated inflammation is desirable. Chronic therapy by infusion of recombinant GMP-140 fragments may also be feasible in some circumstances.

The same principles operate in the interaction of GMP-140 with complement proteins or with protein S. Inhibition of binding reactions with these proteins is similar to binding of GMP-140 to leukocytes. Both promotion and inhibition of the anticoagulant effects of protein S are possible. For example, the anticoagulant effect of protein S may be enhanced by addition of active soluble GMP-140 fragments. Alternatively, if the anticoagulant effect of Protein S is depressed by cell-bound GMP-140, then infusion of soluble GMP-140 is either neutral or can competitively inhibit the anticoagulant activity of the Protein S.

Reperfusion injury is a major problem in clinical cardiology. Therapeutic agents that reduce leukocyte adherence in ischemic myocardium can significantly enhance the therapeutic efficacy of thrombolytic agents. Thrombolytic therapy with agents such as tissue plasminogen activator or streptokinase can relieve coronary artery obstruction in many patients with severe myocardial ischemia prior to irreversible myocardial cell death. However, many such patients still suffer myocardial neurosis despite restoration of blood flow. This "reperfusion injury" is known to be associated with adherence of leukocytes to vascular endothelium in the ischemic zone, presumably in part because of activation of platelets and endothelium by thrombin and cytokines that makes them adhesive for leukocytes (Romson et al., Circulation 67: 1016–1023, 1983). These adherent leukocytes can migrate through the endothelium and destroy ischemic myocardium just as it is being rescued by restoration of blood flow.

There are a number of other common clinical disorders in which ischemia and reperfusion results in organ injury mediated by adherence of leukocytes to vascular surfaces, including strokes; mesenteric and peripheral vascular disease; organ transplantation; and circulatory shock (in this case many organs might be damaged following restoration of blood flow).

Bacterial sepsis and disseminated intravascular coagulation often exist concurrently in critically ill patients. They are associated with generation of thrombin, cytokines, and other inflammatory mediators, activation of platelets and endothelium, and adherence of leukocytes and aggregation of platelets throughout the vascular system. Leukocyte-dependent organ damage is an important feature of these conditions.

Adult respiratory distress syndrome is a devastating pulmonary disorder occurring in patients with sepsis or following trauma, which is associated with widespread adherence and aggregation of leukocytes in the pulmonary circulation. This leads to extravasation of large amounts of plasma into the lungs and destruction of lung tissue, both mediated in large part by leukocyte products.

Two related pulmonary disorders that are often fatal are in immunosuppressed patients undergoing allogeneic bone marrow transplantation and in cancer patients suffering from complications that arise from generalized vascular leakage resulting from treatment with interleukin-2 treated LAK cells (lymphokine-activated lymphocytes). LAK cells are known to adhere to vascular walls and release products that are presumably toxic to endothelium. Although the mechanism by which LAK cells adhere to endothelium is not known, such cells could potentially release molecules that activate endothelium and then bind to endothelium by mechanisms similar to those operative in neutrophils.

Tumor cells from many malignancies (including carcinomas, lymphomas, and sarcomas) can metastasize to distant sites through the vasculature. The mechanisms for adhesion of tumor cells to endothelium and their subsequent migration are not well understood, but may be similar to those of leukocytes in at least some cases. The association of platelets with metastasizing tumor cells has been well described, suggesting a role for platelets in the spread of some cancers.

Platelet-leukocyte interactions are believed to be important in atherosclerosis. Platelets might have a role in recruitment of monocytes into atherosclerotic plaques; the accumulation of monocytes is known to be one of the earliest detectable events during atherogenesis. Rupture of a fully developed plaque may not only lead to platelet deposition and activation and the promotion of thrombus formation, but also the early recruitment of neutrophils to an area of ischemia.

Preferred embodiments of the present invention provide methods for the administration of glycoprotein or antibody for the control of inflammatory response. In one preferred embodiment of the present invention monoclonal antibodies directed against GMP-140 are prepared as described above, or by using other methods known to those skilled in the art.

In addition to screening for monoclonal antibodies that react with purified GMP-140, antibodies that inhibit specific functions of GMP-140 can be identified with specific blocking assays. For example, the assay in which neutrophils bind to immobilized GMP-140 on plastic wells can be used to identify monoclonal antibodies that inhibit the binding; this assay is straightforward and was used to demonstrate the blocking efficacy of polyclonal antibodies to GMP-140. Monoclonal antibodies can also be screened for inhibition of binding of leukocytes to activated platelets or endothelium by published assays. Inhibition of binding of GMP-140 to complement proteins or protein S can be assessed by ELISA procedures or radioimmunoassays known to those skilled in the art.

The GMP-140 specific antibody is administered locally at a wound or inflammatory site by topical application of a solution or cream; by implanting a drug delivery device; or by injection. Additionally, the antibody may be given systemically in whole body dosages by subcutaneous or intravenous injection.

The administration of the antibody results in the formation of a complex between GMP-140 on the endothelial or platelet cell surface and the GMP-140 specific antibody. The binding of the antibody to GMP-140 masks the glycoprotein and reduces the level of GMP-140 available to participate in adhesion or binding of leukocytes and complement components. A reduction in binding or adhesion reduces subsequent tissue damage and minimizes inflammatory response. Clinical applications of this method include post-myocardial infarct treatment and administrations to patients in shock.

In another preferred embodiment of the present invention the glycoprotein, or an active fragment thereof, is administered to the patient to reduce inflammatory response. Membrane bound, soluble, recombinantly derived or any therapeutically active fragment of GMP-140 is purified by affinity chromatography as described above, or by other methods known to those skilled in the arts. Administration of the glycoprotein, either locally or in whole body dosages, results in the formation of complexes on the surface of leukocytes (or other cells which have GMP-140 ligands on their surface.) Additionally, GMP-140 binding proteins will be complexed by the exogenously administered glycoprotein. Consequently, components of the inflammatory response system will be effectively blocked and thus unable to participate in tissue damage at the site of inflammation.

The criteria for assessing response to therapeutic modalities employing antibodies to GMP-140 is dictated by the specific condition and will generally follow standard medical practices. For example, the criteria for the effective dosage to prevent extension of myocardial infarction would be determined by one skilled in the art by looking at marker enzymes of myocardial necrosis in the plasma, by monitoring the electrocardiogram, vital signs, and clinical response. For treatment of acute respiratory distress syndrome, one would examine improvements in arterial oxygen, resolution of pulmonary infiltrates, and clinical improvement as measured by lessened dyspnea and tachypnea. For treatment of patients in shock (low blood pressure), the effective dosage would be based on the clinical response and specific measurements of function of vital organs such as the liver and kidney following restoration of blood pressure. Neurologic function would be monitored in patients with stroke. Specific tests are used to monitor the functioning of transplanted organs; for example, serum creatinine, urine flow, and serum electrolytes in patients undergoing kidney transplantation.

Detection of Disease Disorders

In another embodiment of the present invention monoclonal antibodies against GMP-140 are used for the detection of human disorders in which GMP-140 might be defective. Such disorders would most likely be seen in patients with increased susceptibility to infections in which leukocytes might not be able to bind to activated platelets or endothelium. Other patients might have bleeding defects due to unstable platelet aggregates arising from deficient GMP-140 levels. Cells to be tested, usually platelets, are collected by standard medically approved techniques and screened for the presence of GMP-140 using the monoclonal antibody S12 or other monoclonal antibodies to GMP-140. The antibody is labeled radioactively, with fluorescein, enzymatically, or by other methods known to those skilled in the arts, and incubated with the appropriately treated cells or cell lysate. Detection systems include ELISA procedures, binding of radiolabeled antibody to immobilized activated cells, flow cytometry, or other methods known to those skilled in the arts. The levels of the soluble form of GMP-140 can also be measured in plasma and in serum using standard ELISA or radioimmunoassay procedures. In this manner the total GMP-140, and soluble GMP-140 of an individual can be determined and compared with levels of GMP-140 in healthy individuals.

In yet another embodiment of the present invention labeled GMP-140 is used to detect defects in molecules binding to GMP-140. Such disorders would most likely be seen in patients with increased susceptibility to infections in which leukocytes would have defective binding to platelets and endothelium because of deficient leukocyte ligands for GMP-140. GMP-140 or an active fragment thereof, is purified as described above and labeled radioactively, with a fluorescent tag, enzymatically, or with electron dense material such as gold for electron microscopy. The cells to be examined, usually leukocytes, are incubated with labeled GMP-140 and binding assessed by methods described above with antibodies to GMP-140, or by other methods known to those skilled in the art. If ligands for GMP-140 are also found in the plasma, they can also be measured with standard ELISA or radioimmunoassay procedures, using labeled GMP-140 instead of antibody as the detecting reagent. Genetic or acquired disorders in which there are defective components that bind to GMP-140 can thus be diagnosed using this method.

In still another embodiment of the present invention genetic disorders of glycoprotein production, processing, or tissue-specific presentation of GMP-140 can be detected through the use of GMP-140 nucleic acid sequences. GMP-140 cDNA probes or DNA fragments prepared from the probes can be used for hybridization analysis. Genomic DNA from an individual is isolated and hybridized, either by dot blot or by Southern hybridization, with GMP-140 specific DNA probes in order to detect alterations (mutations, insertions, or deletions) in the individual's GMP-140 related genes.

Alternatively, messenger RNA from an individual is isolated from either platelets or endothelial cells and analyzed by Northern hybridization using GMP-140 specific DNA sequences. This method determines the actual levels of mRNA transcripts for GMP-140 as well as the size of the transcript. Because of the small quantities of mRNA present in circulating platelets, a useful variant is to amplify the sequence of interest by using the polymerase chain reaction. Oligonucleotides at each end of the GMP-140 sequence of interest are incubated with platelet RNA and reverse transcriptase is added. After the initial reaction, the polymerase chain reaction is continued for many cycles with heat-stable Tac DNA polymerase until large amounts of DNA corresponding to the mRNA transcript are generated. This DNA can be analyzed for size by standard agarose gel electrophoresis, by restriction mapping, and by hybridization with specific GMP-140 DNA sequences.

Modifications and variations of the present invention, methods for modulating binding reactions involving GMP-140, will be obvious to those skilled in the art from the foregoing detailed description. Such modifications and variations are intended to come within the scope of the appended claims.

I claim:

1. A purified soluble form of human granule membrane protein 140 which lacks an amino acid sequence comprising a transmembrane domain and which is effective in inhibiting leukocyte adherence mediated by granule membrane protein 140.

2. The soluble granule membrane protein 140 of claim 1 wherein the amino acid sequence of the soluble granule membrane protein 140 comprises amino acids 1–722 of FIGS. 2 and 2A.

3. The soluble granule membrane protein 140 of claim 1 obtained by expressing the DNA encoding the soluble granule membrane protein 140 in a non-human host cell.

4. The soluble human granule membrane protein 140 of claim 1 wherein the amino acid sequence thereof comprises amino acids 1–528 and 591–722 of FIGS. 2 and 2A.

5. A purified soluble recombinant form of human granule membrane protein 140 which is effective in inhibiting granule membrane protein-140-mediated leukocyte adherence said soluble recombinant form of human granule membrane protein 140 lacking an amino acid sequence which functions as a transmembrane domain.

* * * * *

UNITED STATES PATENT AND TRADEMARK OFFICE
CERTIFICATE OF CORRECTION

PATENT NO. : 5,767,241
DATED : June 16, 1998
INVENTOR(S) : Rodger P. McEVER

It is certified that error appears in the above-identified patent and that said Letters Patent is hereby corrected as shown below:

On the title page,

"OTHER PUBLICATIONS", delete "Bevilacqua, M.P., et al., *Science*, vol. 242, pp. 1160-1165 (Mar. 3, 1989)." and substitute therefor --Bevilacqua, M.P., et al., *Science*, vol. 243, pp. 1160-1165 (Mar. 3, 1989).--.

Col. 7: line 46, delete "-19,500 rpm" and substitute therefor --19,500 rpm--.

Col. 9: line 60, delete "lambdaGMPE-" and substitute therefor --lambdaGMPE1- --.

line 61, delete "1-lambdaGMPE3," and substitute therefor --lambdaGMPE3--.

Signed and Sealed this

First Day of June, 1999

Attest:

Attesting Officer

Q. TODD DICKINSON

*Acting Commissioner of Patents and Trademarks*